(12) United States Patent
Van Egmond et al.

(10) Patent No.: US 7,060,866 B2
(45) Date of Patent: *Jun. 13, 2006

(54) HIGH PRESSURE SEPARATION OF DIMETHYL ETHER FROM AN OLEFIN STREAM

(75) Inventors: Cor F. Van Egmond, Pasadena, TX (US); Jeffrey L. Brinen, League City, TX (US); James R. Lattner, Seabrook, TX (US); Michael Peter Nicoletti, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 238 days.

This patent is subject to a terminal disclaimer.

(21) Appl. No.: 10/125,138

(22) Filed: Apr. 18, 2002

(65) Prior Publication Data

US 2003/0199724 A1    Oct. 23, 2003

(51) Int. Cl.
*C07G 7/10*      (2006.01)
*C07G 7/08*      (2006.01)
*C07G 1/02*      (2006.01)

(52) U.S. Cl. .................. 585/833; 585/836; 585/638; 585/639; 585/640; 585/809; 585/864

(58) Field of Classification Search ............... 585/809, 585/833, 807, 899, 836, 638, 639, 640, 864
See application file for complete search history.

(56) References Cited

U.S. PATENT DOCUMENTS

| | | | |
|---|---|---|---|
| 4,474,647 A | 10/1984 | Asselineau et al. | 203/49 |
| 4,499,327 A | 2/1985 | Kaiser | 585/640 |
| 5,090,977 A | 2/1992 | Strack et al. | 62/23 |
| 5,336,841 A | 8/1994 | Adams | 585/834 |
| 5,609,734 A | 3/1997 | Streicher et al. | 203/39 |
| 5,720,929 A | 2/1998 | Minkkinen et al. | 422/194 |
| 5,914,433 A | 6/1999 | Marker | 585/313 |
| 6,121,504 A | 9/2000 | Kuechler et al. | 585/640 |
| 6,559,248 B1 * | 5/2003 | Hendriksen et al. | 526/77 |

FOREIGN PATENT DOCUMENTS

EP     0 060 103     4/1985

OTHER PUBLICATIONS

Eng, Curtis N., et al, "Integration of the UOP/HYDRO MTO Process into Ethylene Plants," *10th Ethylene Producers'Conference*, 1998, pp. 54-85.

* cited by examiner

*Primary Examiner*—Tam M. Nguyen (57) ABSTRACT

Disclosed is a method of removing dimethyl ether from an ethylene and/or propylene containing stream. Dimethyl ether is removed at a high pressure, preferably in a distillation column. The high pressure separation has the benefit of providing a relatively low bottoms temperature separation, while allowing for recovery of a highly concentrated ethylene and/or propylene stream.

32 Claims, 2 Drawing Sheets

Fig. 1

Fig. 2

HIGH PRESSURE SEPARATION OF DIMETHYL ETHER FROM AN OLEFIN STREAM

FIELD OF THE INVENTION

This invention is directed to a method of removing oxygenated contaminants from an olefin stream. In particular, this invention is directed to a method of removing dimethyl ether from an ethylene and/or propylene containing stream.

BACKGROUND OF THE INVENTION

Olefins, particularly $C_2$ and $C_3$ olefins, are desirable as a feed source for making derivative products such as oligomers, e.g., higher olefins, and polymers such as polyethylene and polypropylene. Olefin feed sources have traditionally been produced by cracking petroleum feedstocks.

U.S. Pat. No. 5,090,977 discloses a method of making olefins by steam cracking. The method includes separating the olefin product into methane, hydrogen, ethane, ethylene, propylene and $C_5+$ streams. The disclosed separation preferentially produces propylene, and no propane, butane, butene, or butadiene streams are produced.

Oxygenate feed stocks, however, are becoming an alternative to petroleum feed stocks for making olefins, particularly large quantities of ethylene and propylene for the production of higher olefins and plastic materials. In general, the olefins are formed by contacting the oxygenate components with a molecular sieve catalyst to catalytically convert the oxygenates to olefins.

For example, U.S. Pat. No. 4,499,327, discloses a process for making olefins from methanol using any of a variety of silicoaluminophosphate (SAPO) molecular sieve catalysts. The process is carried out at a temperature between 300° C. and 500° C., a pressure between 0.1 atmosphere to 100 atmospheres, and a weight hourly space velocity (WHSV) of between 0.1 and 40 $hr^{-1}$. The process is highly selective for making ethylene and propylene.

U.S. Pat. No. 6,121,504 also discloses a method of making olefin product from oxygenate feed using molecular sieve catalysts. Water and other unwanted by-products are removed from the olefin product by contacting with a quench medium. After contacting with the quench medium, a light product fraction is obtained which comprises the desired olefins, but also includes dimethyl ether, methane, CO, $CO_2$, ethane, propane, and other minor components such as water and unreacted oxygenate feedstock.

In order to further process olefins, it is often necessary to reduce or remove undesirable by-products that are present in the olefin composition. For example, U.S. Pat. No. 4,474,647 discloses that dimethyl ether can adversely impact the oligomerization of certain olefins. The patent describes a process for removing dimethyl ether from a $C_4$ and/or $C_5$ olefin stream using distillation. The stream is distilled and separated into an overhead and a bottoms stream. The overhead stream contains dimethyl ether, water, and various hydrocarbons, and the bottoms stream contains purified olefins.

U.S. Pat. No. 5,914,433 discloses a method of making an olefin composition, and a system for removing non-olefin by-products such as $CO_2$. A dewatered olefin composition is washed with caustic to remove $CO_2$, and the washed olefin composition is dried to reduce water added as a result of the caustic wash.

U.S. Pat. No. 5,720,929 discloses a process which includes making isobutylene from isobutane. The isobutylene is cooled and water is stripped from the product. Additional water is removed by washing the product with methanol.

Eng et al., "Integration of the UOP/HYDRO MTO Process into Ethylene Plants," 10th Ethylene Producers'Conference, 1998, disclose a flow scheme for making an olefin composition from methanol. The flow scheme shows a deethanizer-first flow process.

EP-B 1-0 060 103 discloses a process for extracting dimethyl ether from a vapor stream containing ethylene and propylene using a methanol wash system. The methanol wash removes a substantial amount of the dimethyl ether, but also removes a significant amount of the ethylene and propylene.

Additional methods of removing undesirable components from olefin streams are sought. In particular, methods for removing oxygenated hydrocarbons, particularly dimethyl ether, as well as $CO_2$ and water down to the ppm level in olefin product streams, and without removing significant amounts of olefin, are sought.

SUMMARY OF THE INVENTION

In this invention, dimethyl ether is separated from an olefin stream containing ethylene and/or propylene using high pressure separation, preferably high pressure distillation. In one embodiment, the invention provides a method of separating dimethyl ether from an olefin stream which comprises providing an olefin stream containing ethylene, ethane, propylene, propane, and dimethyl ether. The provided stream is separated into a first fraction and a second fraction at a pressure of at least 200 psig. The first fraction contains at least a majority of the ethylene and propylene present in the olefin stream, and the second fraction contains at least a majority of the dimethyl ether present in the olefin stream. In another embodiment, the provided olefin stream further contains water in an amount not greater than about 15,000 wppm.

The invention is particularly effective on olefin streams which contain at least about 500 wppm dimethyl ether. Preferably, the olefin stream contains not greater than about 50 wt % dimethyl ether.

In one embodiment, the separation is such that the first fraction contains at least a majority of the propane present in the olefin stream, and preferably not greater than about 100 wppm dimethyl ether. The separation can be such that a majority of the propane present in the olefin stream can be either in the first or second fraction. The separation can also be such that a majority of propadiene, which can also be present in the olefin stream, can be either in the first or second fraction. To obtain very high purity propylene streams from the olefin stream, it is preferred that a majority of any propadiene and propane present in the olefin feed be separated out in the second fraction.

In another embodiment, the olefin stream is separated into the first fraction and the second fraction in a distillation column. Preferably, water absorbent is added to the distillation column. Water absorbent can be added to the distillation column at a molar ratio of water absorbent to total olefin stream to be separated of from about 4:1 to about 1:5,000.

In yet another embodiment of the invention, the first fraction is acid gas treated. The acid gas treated stream can subsequently be water washed and contacted with solid adsorbent material.

The ethylene and propylene separated from the olefin stream can be used in any ethylene or propylene derivative process, due to the high quality of the recovered streams. Preferred embodiments include polymerization into polyethylene and polypropylene.

In another embodiment, the invention provides a method of separating dimethyl ether from an olefin stream which comprises contacting oxygenate with a molecular sieve catalyst to form an olefin stream, wherein the olefin stream contains ethylene, ethane, propylene, propane, and dimethyl ether. The olefin stream is separated into a first fraction and a second fraction at a pressure of at least 200 psig. The first fraction contains at least a majority of the ethylene and propylene present in the olefin stream, and the second fraction contains at least a majority of the dimethyl ether present in the olefin stream.

In one embodiment of the invention, the olefin stream formed from contacting the oxygenate with the molecular sieve catalyst is contacted with water absorbent prior to separating into the first and second fraction. It is desired that the water absorbent be contacted with the olefin stream at a molar ratio of water absorbent to total olefin of about 1:2 to about 1:200. Preferably, the olefin stream contacted with the water absorbent contains water in an amount not greater than about 15,000 wppm.

The invention further provides a method of separating dimethyl ether from an olefin stream which comprises contacting oxygenate with a molecular sieve catalyst to form an olefin stream, wherein the olefin stream contains ethylene, ethane, propylene, propane, dimethyl ether and water. The water is then removed from the olefin stream so that the olefin stream contains less than about 15,000 wppm water. The olefin stream containing less than about 15,000 wppm water is then separated into a first fraction and a second fraction at a pressure of at least 200 psig, wherein the first fraction contains at least a majority of the ethylene and propylene present in the olefin stream, and the second fraction contains at least a majority of the dimethyl ether present in the olefin stream.

The invention also provides a method of separating dimethyl ether from an olefin stream which comprises providing an olefin stream containing ethylene, ethane, propylene, propane, propadiene and dimethyl ether. The olefin stream is separated into a first fraction containing at least a majority of the ethylene and propylene present in the olefin stream, and a second fraction containing at least a majority of the dimethyl ether and propadiene present in the olefin stream. The separation is performed at a pressure of at least 200 psig and such that the second fraction is at a temperature of not greater than about 250° F.

BRIEF DESCRIPTION OF THE DRAWINGS

Various embodiments of the overall invention are shown by way of example in the attached Figures, wherein.

DETAILED DESCRIPTION OF THE INVENTION

This invention provides a method for removing oxygenated hydrocarbon components such as dimethyl ether from an olefin stream. It is desirable to remove such components, since they may poison catalysts that are used to further process olefins in the olefin stream. The invention is particularly beneficial for removing dimethyl ether from an ethylene and/or propylene stream so that the ethylene and/or propylene can be polymerized without poisoning catalyst used in the polymerization reaction.

In this invention, oxygenated contaminants, particularly including dimethyl ether, are removed from the provided olefin stream at high pressure. An advantage of using a high pressure separation is that separation of olefins can be accomplished at higher temperatures. By taking advantage of higher temperature separation, less refrigeration is required to recover lighter olefins such as ethylene and propylene. The practical result is a substantial savings in power.

Another advantage in high pressure separation is that clathrate and free water formation can be more easily controlled in the separation equipment. This is particularly advantageous when distillation columns having internal trays are used as the separation equipment, since internal trays are prone to collect water and clathrates. If an excessive amount of water and/or clathrates are collected, the trays can break apart or collapse, causing severe equipment damage.

In general, the method of this invention comprises providing an olefin stream which contains ethylene, ethane, propylene, propane, and dimethyl ether, then separating at least a majority, i.e., greater than 50%, of the dimethyl ether present in the olefin stream. The olefin stream can come from any conventional source. However, this invention is particularly effective in separating dimethyl ether from olefin streams made from an oxygenate to olefin process.

In one embodiment, the olefin stream that is provided comprises not greater than about 50 wt % dimethyl ether, preferably not greater than about 20 wt % dimethyl ether, more preferably not greater than about 10 wt % dimethyl ether, and most preferably not greater than about 5 wt % dimethyl ether. Of course, for dimethyl ether to be removed from the olefin stream, some measurable about must be present. Desirably, the provided olefins stream will contain at least about 100 wppm dimethyl ether, preferably at least about 500 wppm dimethyl ether, and more preferably at least about 1,000 wppm dimethyl ether.

In another embodiment, the olefin stream that is provided comprises at least about 25 wt % ethylene. Preferably, the provided olefin stream comprises from about 25 wt % ethylene to about 75 wt % ethylene, more preferably from about 30 wt % to about 60 wt %, and most preferably from about 35 wt % to about 50 wt % propylene.

In another embodiment, the olefin stream that is provided also comprises at least about 20 wt % propylene. Preferably, the provided olefin stream comprises from about 20 wt % propylene to about 70 wt % propylene, more preferably from about 25 wt % to about 50 wt % propylene, and most preferably from about 30 wt % to about 40 wt % propylene.

It is desirable that the provided olefin stream contain a relatively low concentration of ethane, preferably a lower concentration of ethane than propane. Preferably, the olefin stream comprises not greater than about 4 wt % ethane, more preferably not greater than about 3 wt % ethane, and most preferably not greater than about 2 wt % ethane.

It is also desirable that the provided olefin stream contain a relatively low concentration of propane. Preferably, the olefin stream comprises not greater than about 5 wt % propane, more preferably not greater than about 4 wt % propane, and most preferably not greater than about 3 wt % propane.

In another embodiment of the invention, the provided olefin stream contains both ethylene and propylene. Desirably, the olefin stream contains at least about 50 wt % ethylene and propylene. Preferably, the olefin stream contains from about 50 wt % to about 95 wt % ethylene and propylene, more preferably from about 55 wt % to about 90 wt % ethylene and propylene, and most preferably from about 60 wt % to about 85 wt % ethylene and propylene.

The provided olefin steam can also contain some amount of water. However, it is desirable that any water present in the olefin stream will be at a concentration such that free water formation (i.e., formation of a separate water phase) or gas hydration does not significantly impede the separation process. Gas hydration results in the formation of clathrate compounds. Such compounds are solids, and these solids can cause significant operational problems in the separation process.

Water that is present in the provided olefin stream should be at a concentration sufficiently low such that a separate water phase is not formed during the separation process. This is particularly important when a distillation column having trays is used to separate the dimethyl ether from the olefin, since a separate water phase formed in the trays will impede mass transfer. Distillation columns having packing are preferred at higher concentrations of water, since such columns will not be prone to collect separate water phases.

It is desirable in this invention that the provided olefin stream contain not greater than about 15,000 wppm water. Preferably the olefin stream contains not greater than about 10,000 wppm water, more preferably not greater than 5,000 wppm water, and most preferably not greater than about 1,000 wppm water.

It is not necessary in this invention that the olefin stream be completely dry. That is, the olefin stream can contain some water. The benefit of the olefin stream containing some amount of water is that additional and/or complex drying equipment will not be needed before separating the dimethyl ether from the olefin stream. Preferably, the olefin stream contains at least about 10 wppm water, more preferably at least about 100 wppm water, and most preferably at least about 200 wppm water.

If an olefin stream contains an unacceptably high concentration of water, a sufficient amount of the water can be removed either prior to or during separation of the dimethyl ether using a water absorbent. Examples of water absorbents include alcohols, amines, amides, nitriles, heterocyclic nitrogen containing compounds, or a combination of any of the preceding. Either monohydric alcohols or polyhydric alcohols can be used as the alcohol absorbent. Specific examples of absorbents include methanol, ethanol, propanol, ethylene glycol, diethylene glycol, triethylene glycol, ethanolamine, diethanolamine, triethanolamine, hindered cyclic amines, acetonitrile, n-methylpyrrolidone, dimethyl formamide, and combinations thereof.

To obtain a substantial degree of effectiveness, the water absorbent should contain little non-water absorbing components. For example, the water absorbent should contain at least about 75 wt % water absorbing components. Desirably, the water absorbent contains at least about 90 wt %, preferably at least about 95 wt %, and most preferably at least about 98 wt % water absorbent.

When a water absorbent is used to reduce the concentration of water in the olefin stream prior to separation of the dimethyl ether, a wash type of process using a wash vessel can be used. In essence, a wash process is one in which the olefin stream is contacted with water absorbent such that a substantial amount of the water is removed, i.e., washed out, from the olefin stream. The amount of absorbent added to the wash vessel should be sufficient to substantially reduce free water formation (i.e., formation of a separate liquid phase), particularly in the vessel in which the separation of the dimethyl ether from the olefin takes place. In this embodiment, it is desirable that water absorbent be added to the wash vessel at a mole ratio of absorbent compound to total olefin feed to the wash vessel of about 1:2 to about 1:200. Preferably, the absorbent is added at a mole ratio of from about 1:5 to about 1:100, and more preferably from about 1:10 to about 1:50.

Although the olefin stream can come from any conventional source which contains dimethyl ether, the invention is particularly suited to removing dimethyl ether from olefin streams made from an oxygenate to olefin process. In one embodiment of this invention, an olefin stream containing dimethyl ether is obtained by contacting oxygenate feedstock with a molecular sieve catalyst.

In a preferred embodiment of the process of the invention, the oxygenate feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts. Non-limiting examples of oxygenates include methanol, ethanol, n-propanol, iso-propanol, methyl ethyl ether, dimethyl ether, diethyl ether, di-isopropyl ether, formaldehyde, dimethyl carbonate, dimethyl ketone, acetic acid, and mixtures thereof. In the most preferred embodiment, the feedstock is selected from one or more of methanol, ethanol, dimethyl ether, diethyl ether or a combination thereof, more preferably methanol and dimethyl ether, and most preferably methanol.

The feedstock, in one embodiment, contains one or more diluent(s), typically used to reduce the concentration of the feedstock, and are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25. In one embodiment, other hydrocarbons are added to a feedstock either directly or indirectly, and include olefin(s), paraffin(s), aromatic(s) (see for example U.S. Pat. No. 4,677,242, addition of aromatics) or mixtures thereof, preferably propylene, butylene, pentylene, and other hydrocarbons having 4 or more carbon atoms, or mixtures thereof.

Molecular sieves capable of converting an oxygenate to an olefin compound include zeolite as well as non-zeolite molecular sieves, and are of the large, medium or small pore type. Non-limiting examples of these molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof, the medium pore molecular sieves, AFO, AEL, EUO, HEU, FER, MEL, MFI, MTW, MTT, TON, and substituted forms thereof; and the large pore molecular sieves, EMT, FAU, and substituted forms thereof. Other molecular sieves include ANA, BEA, CFI, CLO, DON, GIS, LTL, MER, MOR, MWW and SOD. Non-limiting examples of the preferred molecular sieves, particularly for converting an oxygenate containing feedstock into olefin(s), include AEL, AFY, BEA, CHA, EDI, FAU, FER, GIS, LTA, LTL, MER, MFI, MOR, MTT, MWW, TAM and TON. In one preferred embodiment, the molecular sieve of the invention has an AEI topology or a CHA topology, or a combination thereof, most preferably a CHA topology.

Molecular sieve materials all have 3-dimensional, four-connected framework structure of corner-sharing $TO_4$ tetrahedra, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition*, Volume 137, pages 1–67, Elsevier Science, B.V., Amsterdam, Netherlands (2001).

The small, medium and large pore molecular sieves have from a 4-ring to a 12-ring or greater framework-type. In a preferred embodiment, the molecular sieves have 8-, 10- or 12-ring structures or larger and an average pore size in the range of from about 3 Å to 15 Å. In the most preferred embodiment, the molecular sieves of the invention, preferably silicoaluminophosphate molecular sieves, have 8-rings and an average pore size less than about 5 Å, preferably in the range of from 3 Å to about 5 Å, more preferably from 3 Å to about 4.5 Å, and most preferably from 3.5 Å to about 4.2 Å.

Molecular sieves, particularly zeolitic and zeolitic-type molecular sieves, preferably have a molecular framework of one, preferably two or more corner-sharing $[TO_4]$ tetrahedral units, more preferably, two or more $[SiO_4]$, $[AlO_4]$ and/or $[PO_4]$ tetrahedral units, and most preferably $[SiO_4]$, $[AlO_4]$ and $[PO_4]$ tetrahedral units. These silicon, aluminum, and phosphorous based molecular sieves and metal containing silicon, aluminum and phosphorous based molecular sieves have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 ($AlPO_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851, 106 (CrAPO), U.S. Pat. Nos. 4,758,419, 4,882,038, 5,434, 326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500, 651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit $[QO_2]$), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference.

Other molecular sieves include those described in EP-0 888 187 B1 (microporous crystalline metallophosphates, $SAPO_4$ (UIO-6)), U.S. Pat. No. 6,004,898 (molecular sieve and an alkaline earth metal), U.S. patent application Ser. No. 09/511,943 filed Feb. 24, 2000 (integrated hydrocarbon co-catalyst), PCT WO 01/64340 published Sep. 7, 2001 (thorium containing molecular sieve), and R. Szostak, *Handbook of Molecular Sieves*, Van Nostrand Reinhold, New York, N.Y. (1992), which are all herein fully incorporated by reference.

The more preferred silicon, aluminum and/or phosphorous containing molecular sieves, and aluminum, phosphorous, and optionally silicon, containing molecular sieves include aluminophosphate (ALPO) molecular sieves and silicoaluminophosphate (SAPO) molecular sieves and substituted, preferably metal substituted, ALPO and SAPO molecular sieves. The most preferred molecular sieves are SAPO molecular sieves, and metal substituted SAPO molecular sieves. In an embodiment, the metal is an alkali metal of Group IA of the Periodic Table of Elements, an alkaline earth metal of Group IIA of the Periodic Table of Elements, a rare earth metal of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as $[MeO_2]$, and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. Patents mentioned above, is represented by the empirical formula, on an anhydrous basis:

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIB, VIIB, VIIIB and Lanthanide's of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01.

In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and ALPO molecular sieves used in the invention include one or a combination of SAPO-5, SAPO-8, SAPO-11, SAPO-16, SAPO-17, SAPO-18, SAPO-20, SAPO-3 1, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof. The more preferred zeolite-type molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-1 8, and metal containing molecular sieves thereof.

In an embodiment, the molecular sieve is an intergrowth material having two or more distinct phases of crystalline structures within one molecular sieve composition. In particular, intergrowth molecular sieves are described in the U.S. patent application Ser. No. 09/924,016 filed Aug. 7, 2001 and PCT WO 98/15496 published Apr. 16, 1998, both of which are herein fully incorporated by reference. In another embodiment, the molecular sieve comprises at least one intergrown phase of AEI and CHA framework-types. For example, SAPO-18, ALPO-18 and RUW-18 have an AEI framework-type, and SAPO-34 has a CHA framework-type.

In one embodiment, the molecular sieves used in the invention are combined with one or more other molecular sieves. In another embodiment, the preferred silicoaluminophosphate or aluminophosphate molecular sieves, or a combination thereof, are combined with one more of the following non-limiting examples of molecular sieves described in the following: Beta (U.S. Pat. No. 3,308,069), ZSM-5 (U.S. Pat. Nos. 3,702,886, 4,797,267 and 5,783,321), ZSM-11 (U.S. Pat. No. 3,709,979), ZSM-12 (U.S. Pat. No. 3,832,449), ZSM-12 and ZSM-38 (U.S. Pat. No. 3,948,758), ZSM-22 (U.S. Pat. No. 5,336,478), ZSM-23 (U.S. Pat. No. 4,076,842), ZSM-34 (U.S. Pat. No. 4,086,186), ZSM-35 (U.S. Pat. No. 4,016,245, ZSM-48 (U.S. Pat. No. 4,397,827), ZSM-58 (U.S. Pat. No. 4,698,217), MCM-1 (U.S. Pat. No. 4,639,358), MCM-2 (U.S. Pat. No. 4,673,559), MCM-3 (U.S. Pat. No. 4,632,811), MCM-4 (U.S. Pat. No. 4,664,897), MCM-5 (U.S. Pat. No. 4,639,357), MCM-9 (U.S. Pat. No. 4,880,611), MCM-10 (U.S. Pat. No. 4,623,527), MCM-14 (U.S. Pat. No. 4,619,818), MCM-22 (U.S. Pat. No. 4,954,325), MCM-41 (U.S. Pat. No. 5,098,684), M-41S (U.S. Pat. No. 5,102,643), MCM-48 (U.S. Pat. No. 5,198,203), MCM-49 (U.S. Pat. No. 5,236,575), MCM-56 (U.S. Pat. No. 5,362,697), ALPO-11 (U.S. Pat. No. 4,310,440), titanium aluminosilicates (TASO), TASO-45 (EP-A-0 229,-295), boron silicates (U.S. Pat. No. 4,254,297), titanium aluminophosphates (TAPO) (U.S. Pat. No. 4,500,651), mixtures of ZSM-5 and ZSM-11 (U.S. Pat. No. 4,229,424), ECR-18 (U.S. Pat. No. 5,278,345), SAPO-34 bound ALPO-5 (U.S. Pat. No. 5,972,203), PCT WO 98/57743 published Dec. 23, 1988 (molecular sieve and Fischer-Tropsch), U.S. Pat. No. 6,300,535 (MFI-bound zeolites), and mesoporous molecular sieves (U.S. Pat. Nos. 6,284,696, 5,098,684, 5,102,643 and 5,108,725), which are all herein fully incorporated by reference.

The molecular sieves are made or formulated into catalysts by combining the synthesized molecular sieves with a binder and/or a matrix material to form a molecular sieve catalyst composition or a formulated molecular sieve catalyst composition. This formulated molecular sieve catalyst composition is formed into useful shape and sized particles by conventional techniques such as spray drying, pelletizing, extrusion, and the like.

There are many different binders that are useful in forming the molecular sieve catalyst composition. Non-limiting examples of binders that are useful alone or in combination include various types of hydrated alumina, silicas, and/or other inorganic oxide sol. One preferred alumina containing sol is aluminum chlorhydrol. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide matrix component. For example, an alumina sol will convert to an aluminum oxide matrix following heat treatment.

Aluminum chlorhydrol, a hydroxylated aluminum based sol containing a chloride counter ion, has the general formula of $Al_mO_n(OH)_oCl_p \cdot x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7 \cdot 12(H_2O)$ as is described in G. M. Wolterman, et al., Stud. Surf. Sci. and Catal., 76, pages 105–144 (1993), which is herein incorporated by reference. In another embodiment, one or more binders are combined with one or more other non-limiting examples of alumina materials such as aluminum oxyhydroxide, γ-alumina, boehmite, diaspore, and transitional aluminas such as α-alumina, β-alumina, γ-alumina, δ-alumina, ε-alumina, κ-alumina, and ρ-alumina, aluminum trihydroxide, such as gibbsite, bayerite, nordstrandite, doyelite, and mixtures thereof.

In another embodiment, the binders are alumina sols, predominantly comprising aluminum oxide, optionally including some silicon. In yet another embodiment, the binders are peptized alumina made by treating alumina hydrates such as pseudobohemite, with an acid, preferably an acid that does not contain a halogen, to prepare sols or aluminum ion solutions. Non-limiting examples of commercially available colloidal alumina sols include Nalco 8676 available from Nalco Chemical Co., Naperville, Ill., and Nyacol available from The PQ Corporation, Valley Forge, Pa.

The molecular sieve, in a preferred embodiment, is combined with one or more matrix material(s). Matrix materials are typically effective in reducing overall catalyst cost, act as thermal sinks assisting in shielding heat from the catalyst composition for example during regeneration, densifying the catalyst composition, increasing catalyst strength such as crush strength and attrition resistance, and to control the rate of conversion in a particular process.

Non-limiting examples of matrix materials include one or more of: rare earth metals, metal oxides including titania, zirconia, magnesia, thoria, beryllia, quartz, silica or sols, and mixtures thereof, for example silica-magnesia, silica-zirconia, silica-titania, silica-alumina and silica-alumina-thoria.

In an embodiment, matrix materials are natural clays such as those from the families of montmorillonite and kaolins. These natural clays include sabbentonites and those kaolins known as, for example, Dixie, McNamee, Georgia and Florida clays. Non-limiting examples of other matrix materials include: haloysite, kaolinite, dickite, nacrite, or anauxite. In one embodiment, the matrix material, preferably any of the clays, are subjected to well known modification processes such as calcination and/or acid treatment and/or chemical treatment.

In one preferred embodiment, the matrix material is a clay or a clay-type composition, preferably the clay or clay-type composition having a low iron or titania content, and most preferably the matrix material is kaolin. Kaolin has been found to form a pumpable, high solid content slurry, it has a low fresh surface area, and it packs together easily due to its platelet structure. A preferred average particle size of the matrix material, most preferably kaolin, is from about 0.1 µm to about 0.6 µm with a D90 particle size distribution of less than about 1 µm.

In another embodiment, the weight ratio of the binder to the matrix material used in the formation of the molecular sieve catalyst composition is from 0:1 to 1:15, preferably 1:15 to 1:5, more preferably 1:10 to 1:4, and most preferably 1:6 to 1:5. It has been found that a higher sieve content, lower matrix content, increases the molecular sieve catalyst composition performance, however, lower sieve content, higher matrix material, improves the attrition resistance of the composition.

In another embodiment, the formulated molecular sieve catalyst composition contains from about 1% to about 99%, more preferably from about 5% to about 90%, and most preferably from about 10% to about 80%, by weight of the molecular sieve based on the total weight of the molecular sieve catalyst composition.

In another embodiment, the weight percent of binder in or on the spray dried molecular sieve catalyst composition based on the total weight of the binder, molecular sieve, and matrix material is from about 2% by weight to about 30% by weight, preferably from about 5% by weight to about 20% by weight, and more preferably from about 7% by weight to about 15% by weight.

Once the molecular sieve catalyst composition is formed in a substantially dry or dried state, to further harden and/or activate the formed catalyst composition, a heat treatment such as calcination, at an elevated temperature is usually performed. A conventional calcination environment is air that typically includes a small amount of water vapor. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof.

The process for converting a feedstock, especially a feedstock containing one or more oxygenates, in the presence of a molecular sieve catalyst composition of the invention, is carried out in a reaction process in a reactor, where the process is a fixed bed process, a fluidized bed process (includes a turbulent bed process), preferably a continuous fluidized bed process, and most preferably a continuous high velocity fluidized bed process.

The reaction processes can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred reactor type are riser reactors generally described in *Riser Reactor, Fluidization and Fluid-Particle Systems*, pages 48 to 59, F. A. Zenz and D. F. Othmo, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In the preferred embodiment, a fluidized bed process or high velocity fluidized bed process includes a reactor system, a regeneration system and a recovery system. The reactor system preferably is a fluid bed reactor system having a first reaction zone within one or more riser reactor(s) and a second reaction zone within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a zeolite or zeolite-type molecular sieve catalyst composition or coked version thereof is introduced. In one embodiment, the molecular sieve catalyst composition or coked version thereof is contacted with a liquid or gas, or combination thereof, prior to being introduced to the riser reactor(s), preferably the liquid is water or methanol, and the gas is an inert gas such as nitrogen.

In an embodiment, the amount of fresh feedstock fed separately or jointly with a vapor feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapor feedstocks are preferably the same composition, or contain varying proportions of the same or different feedstock with the same or different diluent.

The feedstock entering the reactor system is preferably converted, partially or fully, in the first reactor zone into a gaseous effluent that enters the disengaging vessel along with a coked molecular sieve catalyst composition. In the preferred embodiment, cyclone(s) within the disengaging vessel are designed to separate the molecular sieve catalyst composition, preferably a coked molecular sieve catalyst composition, from the gaseous effluent containing one or more olefin(s) within the disengaging zone. Cyclones are preferred, however, gravity effects within the disengaging vessel will also separate the catalyst compositions from the gaseous effluent. Other methods for separating the catalyst compositions from the gaseous effluent include the use of plates, caps, elbows, and the like.

In one embodiment of the disengaging system, the disengaging system includes a disengaging vessel, typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system. In another embodiment, the stripping zone is in a separate vessel from the disengaging vessel and the gas is passed at a gas hourly superficial velocity (GHSV) of from 1 hr$^{-1}$ to about 20,000 hr$^{-1}$ based on the volume of gas to volume of coked molecular sieve catalyst composition, preferably at an elevated temperature from 250° C. to about 750° C., preferably from about 350° C. to 650° C., over the coked molecular sieve catalyst composition.

The conversion temperature employed in the conversion process, specifically within the reactor system, is in the range of from about 200° C. to about 1,000° C., preferably from about 250° C. to about 800° C., more preferably from about 250° C. to about 750° C., yet more preferably from about 300° C. to about 650° C., yet even more preferably from about 350° C. to about 600° C. most preferably from about 350° C. to about 550° C.

The conversion pressure employed in the conversion process, specifically within the reactor system, is not critical. The conversion pressure is based on the partial pressure of the feedstock exclusive of any diluent therein. Typically the conversion pressure employed in the process is in the range of from about 0.1 kPaa to about 5 MPaa, preferably from about 5 kpaa to about 1 MPaa, and most preferably from about 20 kpaa to about 500 kpaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor. Typically, the WHSV ranges from about 1 hr$^{-1}$ to about 5000 hr$^{-1}$, preferably from about 2 hr$^{-1}$ to about 3000 hr$^{-1}$, more preferably from about 5 hr$^{-1}$ to about 1500 hr$^{-1}$, and most preferably from about 10 hr$^{-1}$ to about 1000 hr$^{-1}$. In one preferred embodiment, the WHSV is greater than 20 hr$^{-1}$, preferably the WHSV for conversion of a feedstock containing methanol and dimethyl ether is in the range of from about 20 hr$^{-1}$ to about 300 hr$^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, which is herein incorporated by reference.

In one preferred embodiment of the process for converting an oxygenate to olefin(s) using a silicoaluminophosphate molecular sieve catalyst composition, the process is operated at a WHSV of at least 20 hr$^{-1}$ and a Temperature Corrected Normalized Methane Selectivity (TCNMS) of less than 0.016, preferably less than or equal to 0.01. See for example U.S. Pat. No. 5,952,538, which is herein fully incorporated by reference.

In another embodiment of the processes for converting an oxygenate such as methanol to one or more olefin(s) using a molecular sieve catalyst composition, the WHSV is from 0.01 hr$^{-1}$ to about 100 hr$^{-1}$, at a temperature of from about 350° C. to 550° C., and silica to Me$_2$O$_3$ (Me is a Group IIIA or VIII element from the Periodic Table of Elements) molar ratio of from 300 to 2500. See for example EP-0 642 485 B1, which is herein fully incorporated by reference.

Other processes for converting an oxygenate such as methanol to one or more olefin(s) using a molecular sieve catalyst composition are described in PCT WO 01/23500 published Apr. 5, 2001 (propane reduction at an average catalyst feedstock exposure of at least 1.0), which is herein incorporated by reference.

According to one embodiment, the conversion of the primary oxygenate, e.g., methanol, is from 90 wt % to 98 wt %. According to another embodiment the conversion of methanol is from 92 wt % to 98 wt %, preferably from 94 wt % to 98 wt %.

According to another embodiment, the conversion of methanol is above 98 wt % to less than 100 wt %. According to another embodiment, the conversion of methanol is from 98.1 wt % to less than 100 wt %; preferably from 98.2 wt % to 99.8 wt %. According to another embodiment, the conversion of methanol is from 98.2 wt % to less than 99.5 wt %; preferably from 98.2 wt % to 99 wt %.

The oxygenate to olefin process forms a substantial amount of water as a by-product. Much of this water can be removed by cooling the olefin stream from the oxygenate reactor to a temperature below the condensation temperature of the water in the stream. Preferably, the temperature of the product stream is cooled to a temperature below the condensation temperature of the oxygenate feed for the oxygenate to olefins process. In certain embodiments, it is desirable to cool the product stream below the condensation temperature of methanol.

A quench column is one type of equipment that is effective in cooling the olefin stream from the oxygenate to olefin reaction process. In a quench column, a quenching fluid is directly contacted with the olefin stream to cool the stream to the desired condensation temperature. Condensation produces a condensed water containing stream, which generally exits the quench column as a bottoms stream. Olefin generally exits the column as an overhead stream. It is this overhead stream that contains dimethyl ether which must be separated according to this invention. If a high concentration of water still remains in the overhead, then absorbents can be used as described above to lower the water concentration further.

In one particular embodiment of the invention, the quenched olefin stream is further processed by compression, preferably multi-staged compression. Two, three, four or more stages can be used, with two or three stages being preferred.

During or after multi-stage compression, the olefin stream can be washed using a water absorbent, as described above, if desired. This wash using water absorbent can mitigate problems related to gas hydration and/or separate water phase formation. Preferably, multi-stage compression using a water absorbent wash between stages is preferred. The dimethyl ether and C$_4$+ hydrocarbon components are then separated from the olefin stream.

In one embodiment of this invention, the olefin stream is separated into a first fraction and a second fraction, with a majority of ethylene and/or propylene being separated in the first fraction and a majority of the dimethyl ether being separated in the second fraction. Desirably, separation is carried out at a pressure of at least about 200 psig (1,480 kPa absolute). Preferably, separation is carried out at a pressure of from about 200 psig (1,480 kPa absolute) to about 290 psig (2,100 kPa absolute), more preferably from about 250 psig (1,825 kPa absolute) to about 290 psig (2,100 kPa absolute).

The actual upper pressure limit of the separation process will typically depend upon the temperature at which the second fraction is separated. The second fraction will contain dimethyl ether and other hydrocarbons having boiling points higher than dimethyl ether, for example $C_4+$ olefins. It is desirable to keep the compounds in the second fraction sufficiently low in temperature so as not to cause chemical degradation or fouling problems in other downstream separation and treating equipment. In one embodiment, separation will be such that the second fraction will have an average temperature of not greater than about 250° F. (121° C.), preferably not greater than about 240° F. (116° C.), more preferably not greater than about 230° F. (110° C.).

In this invention, water absorbent, as described above, can optionally be added to the vessel in which the separation of the oxygenated contaminants from the provided olefin stream is performed. The addition of water absorbent directly to the separation vessel can be of additional beneficial in reducing free water and/or clathrate formation in the vessel.

In one embodiment of the invention, water absorbent is optionally added to the oxygenate separation vessel in an amount sufficient to substantially reduce oxygenate content (e.g., dimethyl ether) or clathrate formation. It is preferred that water absorbent be added to the vessel at a molar ratio of water absorbent to total olefin feed entering the separation vessel of about 4:1 to about 1:5,000. Higher molar ratios of water absorbent to total olefin feed are desirable for reducing oxygenate content; preferably from about 4:1 to about 1:1, more preferably from about 3:1 to about 1.2:1, and most preferably from about 2.5:1 to about 1.5:1. Lower molar ratios of water absorbent to total olefin feed are desirable for reducing clathrate formation; preferably from about 1:1 to about 1:5,000, more preferably from about 1:100 to about 1:4,000, and most preferably from about 1:500 to about 1:3,000.

In one embodiment of this invention, separation is by conventional distillation. Distillation is carried out using a vessel or tower having internal packing or trays that creates a temperature difference from top to bottom of the tower. The upper portion of the tower is the cooler portion, and higher volatile components in the feed exit from the top of the tower.

In this invention it is desirable to obtain high concentrations of ethylene and propylene from an olefin stream containing dimethyl ether. In one embodiment, the dimethyl ether is separated from the ethylene and propylene in the olefin stream. In this embodiment the ethylene and propylene are recovered in a first fraction, and the dimethyl ether is recovered in a second fraction. Typically, the first fraction will be the overhead or side fraction of a distillation column, and the second fraction will be a bottoms fraction or additional side fraction of a distillation column.

In one embodiment of the invention, a majority of the ethylene and propylene in the provided olefin stream will be separated in a first fraction and a majority of the dimethyl ether in the provided olefin stream will be separated in a second fraction. Preferably, the first fraction will contain at least about 75% of the ethylene and propylene in the provided olefin stream, more preferably at least about 85%, and most preferably at least about 95%.

In another embodiment, at least about 75% of the dimethyl ether in the provided olefin stream will be separated out in the second fraction. Preferably, at least about 85% of the dimethyl ether in the provided olefin stream will be separated out in the second fraction, more preferably at least about 95%, and most preferably at least about 99%.

A majority of the propane in the provided olefin stream can be separated out in either the first or second fraction. If the majority of the propane is contained in the first fraction, then there will be less separation of heavier products needed in the second fraction. However, there may be slightly increased levels of dimethyl ether in the first fraction when a majority of the propane is in the first fraction. In this embodiment, at least about 60% of the propane in the provided olefin stream, preferably at least about 70%, and more preferably at least about 80% will be in the first fraction, and the first fraction will contain not greater than about 50 wppm, preferably not greater than about 25 wppm, more preferably not greater than about 10 wppm dimethyl ether, and most preferably not greater than about 5 wppm dimethyl ether.

If a majority of the propane in the provided olefin stream is separated out in the second fraction, then the concentration of dimethyl ether in the first fraction will be significantly lower. In this embodiment, at least about 60% of the propane in the provided olefin stream, preferably at least about 70%, and more preferably at least about 80% will be in the second fraction, and the second fraction will contain not greater than about 25 wppm, preferably not greater than about 15 wppm, more preferably not greater than about 5 wppm ether, and most preferably not greater than about 1 wppm dimethyl ether.

In another embodiment of the invention, the second fraction will also contain some hydrocarbon compounds having four or more carbons. These compounds are also known as $C_4+$ components. The amount of $C_4+$ components in the second fraction can vary, particularly depending upon the amount of propane in the second fraction. For example the second fraction can contain from about 5 wt % to about 90 wt % $C_4+$ components. Preferably, the second fraction contains from about 25 wt % to about 80 wt % $C_4+$ components, more preferably from about 35 wt % to about 75 wt % $C_4+$ components.

It is of further advantage in this invention to operate the separation vessel at a temperature and pressure to separate out of the provided olefin stream at least a majority (i.e., at least 50%) of any propadiene which might be present. In this embodiment, the propadiene would preferably be separated out in the second fraction along with dimethyl ether. Preferably, at least about 75%, more preferably at least about 85%, and most preferably at least about 95% of the propadiene would be separated out. Separating out any propadiene out in this manner would necessarily include separating out a substantial portion of any methyl acetylene which may also be present in the provided olefin stream. This is because methyl acetylene has a lower normal boiling point than propadiene and dimethyl ether. Removing propadiene and methyl acetylene from the provided olefin stream would provide a substantial benefit in that the first fraction containing the ethylene and/or propylene would have a very high concentration of mono-olefimic compounds. Such a stream would need little if any hydro processing, which might typically be needed to reduce the number of diolefins or alkylene compounds recovered in the first fraction.

This invention is particularly advantageous for treating the ethylene and propylene streams contained in the first fraction to remove entrained acid gases such as $CO_2$ which may also be present in such fraction. The advantage is that in this invention the separated ethylene and propylene streams will contain relatively few hydrocarbon components that cause fouling problems in such acid gas treatment systems.

Solid or liquid acid gas treatment systems can be used in this invention. In either system, the acid gas is removed from the ethylene and/or propylene stream in the first fraction by contacting the first fraction with an acid gas absorbent or adsorbent. Examples of such absorbents or adsorbents include amines, potassium carbonate, caustic, alumina, molecular sieves, and membranes, particularly membranes formed of polysulfone, polyimid, polyamide, glassy polymer and cellulose acetate. Solutions containing amines and caustic compounds are preferred, with caustic compounds being more preferred.

Aqueous amine solutions which are useful in this invention can contain any amine compound or compounds suitable for acid gas absorption. Examples include alkanolamines, such as triethanolamine (TEA); methyldiethanolamine (MDEA); diethanolamine (DEA); monoethanolamine (MEA); diisopropanolamine (DIPA); and hydroxyaminoethyl ether (DGA). Effective concentrations can range from about 0.5 to about 8 moles of amine per liter of aqueous solution.

Piperazine and/or monomethylethanolamine (MMEA) can be added to aqueous amine solutions to enhance their absorption capabilities. These additives can be included in the aqueous solution at a concentration of from about 0.04 to about 2 moles per liter of aqueous solution.

Caustic compounds which can be used in this invention are alkaline compounds which are effective in removing acid gas from an olefin stream. Examples of such alkaline compounds include sodium hydroxide and potassium hydroxide.

Following acid gas treating, it is desirable to remove additionally entrained material in the treated ethylene and/or propylene using a water wash. Conventional equipment can be used. It is desirable, however, to further remove additional water from the separated ethylene and/or propylene streams.

In one embodiment of this invention, the ethylene and propylene in the first fraction is water washed, i.e., contacted with a water stream, prior to acid gas treating. This contacting is particularly advantageous when water absorbent is added to the oxygenate separation vessel, as water absorbent may carry over into the first or overhead fraction. Water washing would then be conducted to remove a substantial portion of water absorbent carry over prior to acid gas treating.

This invention further includes an optional drying embodiment. In this embodiment, a solid or liquid drying system can be used to remove water and/or additional oxygenated hydrocarbon from the first fraction.

In the solid drying system, the ethylene and/or propylene having been separated in a first fraction, and optionally acid gas treated and water washed, is contacted with a solid adsorbent to further remove water and oxygenated hydrocarbon to very low levels. Typically, the adsorption process is carried out in one or more fixed beds containing a suitable solid adsorbent.

Adsorption is useful for removing water and oxygenated hydrocarbons to very low concentrations, and for removing oxygenated hydrocarbons that may not normally be removed by using other treatment systems. Preferably, an adsorbent system used as part of this invention has multiple adsorbent beds. Multiple beds allow for continuous separation without the need for shutting down the process to regenerate the solid adsorbent. For example, in a three bed system typically one bed is on-line, one bed is regenerated off-line, and a third bed is on stand-by.

The specific adsorbent solid or solids used in the adsorbent beds depends on the types of contaminants being removed. Examples of solid adsorbents for removing water and various polar organic compounds, such as oxygenated hydrocarbons and absorbent liquids, include aluminas, silica, 3A molecular sieves, 4A molecular sieves, and alumino-silicates. Beds containing mixtures of these sieves or multiple beds having different adsorbent solids can be used to remove water, as well as a variety of oxygenated hydrocarbons.

In this invention, one or more adsorption beds can be arranged in series or parallel. In one example of a series arrangement, a first bed is used to remove the smallest and most polar molecules which are the easiest to remove. Subsequent beds for removing larger less polar oxygenated species are next in series. As a specific example of one type of arrangement, water is first selectively removed using a 3A molecular sieve. This bed is then followed by one or more beds containing one or more less selective adsorbents such as a larger pore molecular sieve e.g. 13x and/or a high surface area active alumina such as Selexorb CD (Alcoa tradename).

In another embodiment, the first bed is a 3.6A molecular sieve capable of selectively removing both water and methanol. This bed can then be followed by one or more 13x or active alumina beds as described above.

The adsorbent beds can be operated at ambient temperature or at elevated temperature as required, and with either upward or downward flow. Regeneration of the adsorbent materials can be carried out by conventional methods including treatment with a stream of a dry inert gas such as nitrogen at elevated temperature.

In the liquid drying system, a water absorbent is used to remove water from the first fraction. The water absorbent can be any liquid effective in removing water from an olefin stream. Preferably, the water absorbent is the same as that previously described.

Preferably the olefin from the adsorption beds contains less than about 100 wppm water, more preferably less than about 10 wppm, and most preferably less than 1 wppm. Preferably less than about 10 wppm dimethyl ether is present in the stream leaving the adsorption beds, more preferably less than about 5 wppm, and most preferably less than about 1 wppm.

The ethylene and propylene streams treated and separated according to this invention can be polymerized to form plastic compositions, e.g., polyolefins, particularly polyethylene and polypropylene. Any conventional process for forming polyethylene or polypropylene can be used. Catalytic processes are preferred. Particularly preferred are metallocene, Ziegler/Natta, aluminum oxide and acid catalytic systems. See, for example, U.S. Pat. Nos. 3,258,455; 3,305, 538; 3,364,190; 5,892,079; 4,659,685; 4,076,698; 3,645, 992; 4,302,565; and 4,243,691, the catalyst and process descriptions of each being expressly incorporated herein by reference. In general, these methods involve contacting the ethylene or propylene product with a polyolefin-forming catalyst at a pressure and temperature effective to form the polyolefin product.

In one embodiment of this invention, the ethylene or propylene product is contacted with a metallocene catalyst to form a polyolefin. Desirably, the polyolefin forming process is carried out at a temperature ranging between about 50° C. and about 320° C. The reaction can be carried out at low, medium or high pressure, being anywhere within the range of about 1 bar to about 3200 bar. For processes carried out in solution, an inert diluent can be used. In this type of operation, it is desirable that the pressure be at a range of from about 10 bar to about 150 bar, and preferably at a temperature range of from about 120° C. to about 250° C. For gas phase processes, it is preferred that the temperature generally be within a range of about 60° C. to 120° C., and that the operating pressure be from about 5 bar to about 50 bar.

In addition to polyolefins, numerous other olefin derivatives may be formed from the ethylene, propylene and $C_4+$ olefins, particularly butylene, separated according to this invention. The olefins separated according to this invention can also be used in the manufacture of such compounds as aldehydes, acids such as $C_2$–$C_{13}$ mono carboxylic acids, alcohols such as $C_2$–$C_{12}$ mono alcohols, esters made from the $C_2$–$C_{12}$ mono carboxylic acids and the $C_2$–$C_{12}$ mono alcohols, linear alpha olefins, vinyl acetate, ethylene dicholoride and vinyl chloride, ethylbenzene, ethylene oxide, cumene, acrolein, allyl chloride, propylene oxide, acrylic acid, ethylene-propylene rubbers, and acrylonitrile, and trimers and dimers of ethylene and propylene. The $C_4+$ olefins, butylene in particular, are particularly suited for the manufacture of aldehydes, acids, alcohols, esters made from $C_5$–$C_{13}$ mono carboxylic acids and $C_5$–$C_{13}$ mono alcohols and linear alpha olefins.

Figure 1:
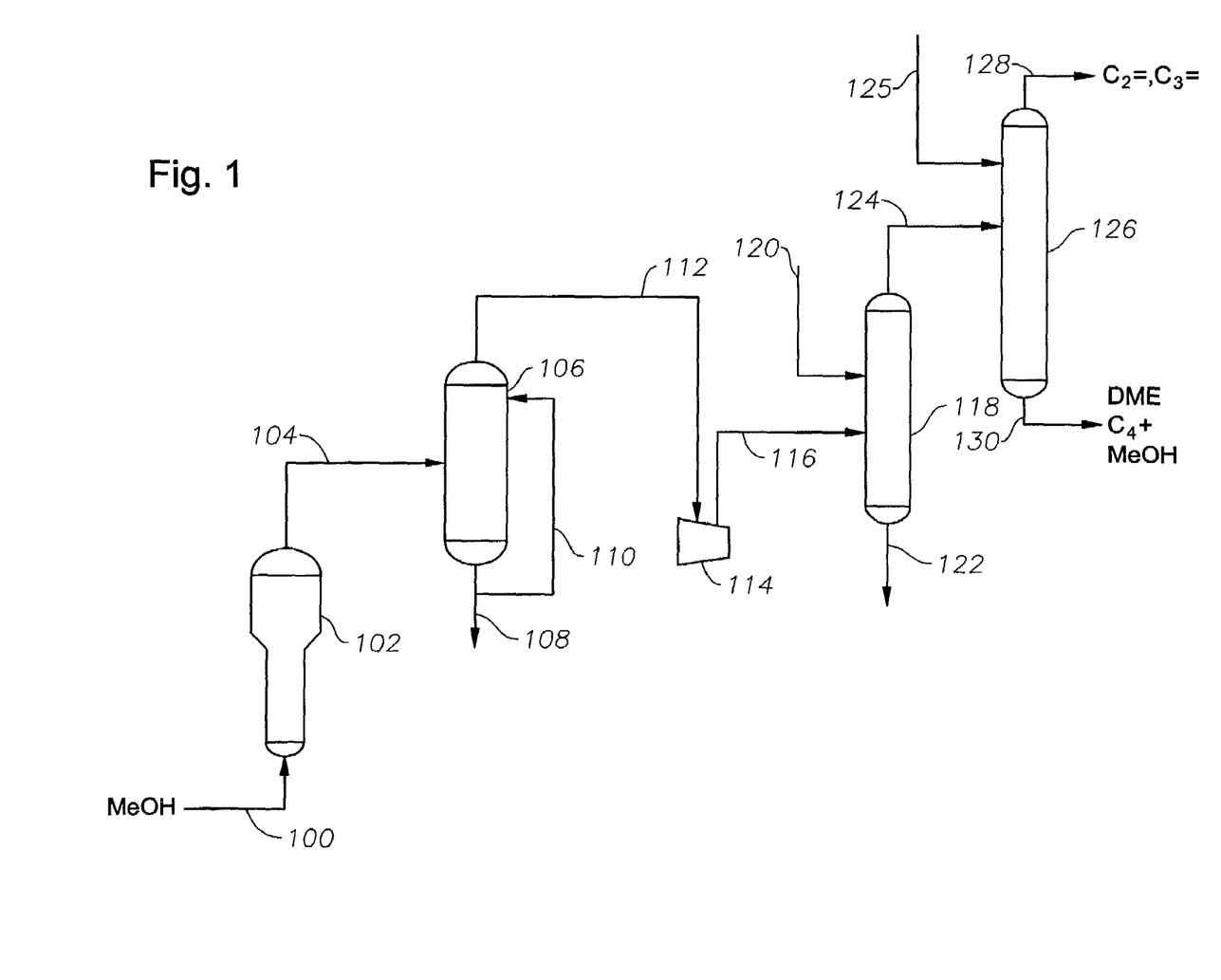
FIG. 1 is a flow diagram showing a process for reacting methanol to form an olefin, with the olefin being separated into a first fraction containing ethylene and propylene and a second fraction containing dimethyl ether and $C_4$+ hydrocarbon components.

One example of separating dimethyl ether from an olefin stream is shown in FIG. 1. This example demonstrates one way of obtaining an ethylene and propylene stream substantially depleted of dimethyl ether, as well as $C_4+$ components. The common factor in this invention, however, is that the dimethyl ether and $C_4+$ components are substantially removed from the ethylene and/or propylene containing stream prior to caustic treatment. This means that both ethylene and propylene can be recovered in a first fraction, with the dimethyl ether and $C_4+$ components being recovered in a second fration. Propane which is present in the olefin stream can be recovered in either the first or second stream, depending upon how low a concentration of dimethyl ether in the first fraction is desired. The ethylene and propylene can then both be recovered and further treated, e.g., caustic wash treated or water wash treated, together or separated and treated separately.

FIG. 1 shows one embodiment in which the olefin to be treated is made in an oxygenate to olefin reaction system. In the Figure, methanol is sent through a line 100 to an oxygenate to olefin reactor 102 where the methanol is converted to an olefin stream comprising methane, ethylene, ethane, propylene, propane, dimethyl ether, $C_4+$ components, water and other hydrocarbon components. The olefin stream is sent through a line 104 to a quench tower 106 where the olefin is cooled and water and other condensable components are condensed.

The condensed components, which comprise a substantial amount of water, are withdrawn from the quench tower 106 through a bottoms line 108. A portion of the condensed components are recycled through a line 110 back to the top of the quench tower 106. The line 110 contains a cooling unit, e.g., heat exchanger, (not shown) to farther cool the condensed components so as to provide a cooling medium to further cool the components in quench tower 106.

Olefin vapor leaves the top portion of quench tower 106 through a line 112. The olefin vapor is compressed in compressor 114 and the compressed olefin is passed through a line 116 to a water absorption column 118. In this embodiment, methanol is used as the water absorbent, and is fed to the top portion of the water absorption column 118 through a line 120. Methanol and entrained water, as well as some oxygenated hydrocarbon, is separated as a bottoms stream though a line 122. Olefin is recovered through a line 124. Optionally, the olefin is sent to an additional compressor (not shown), then is input to a distillation column 126.

The distillation column 126 separates ethylene and propylene, as well as lighter boiling point components from the dimethyl ether and heavier boiling point components, including $C_4+$ components and methanol remaining from the methanol wash. Methanol is optionally added to the distillation column 126 though a line 125 to reduce clathrate and/or free water formation in the distillation column. The ethylene and propylene containing stream exits the distillation column 126 through a line 128, and the heavier boiling point components which include the dimethyl ether and $C_4+$ components exit the distillation column 126 through a line 130.

Figure 2:
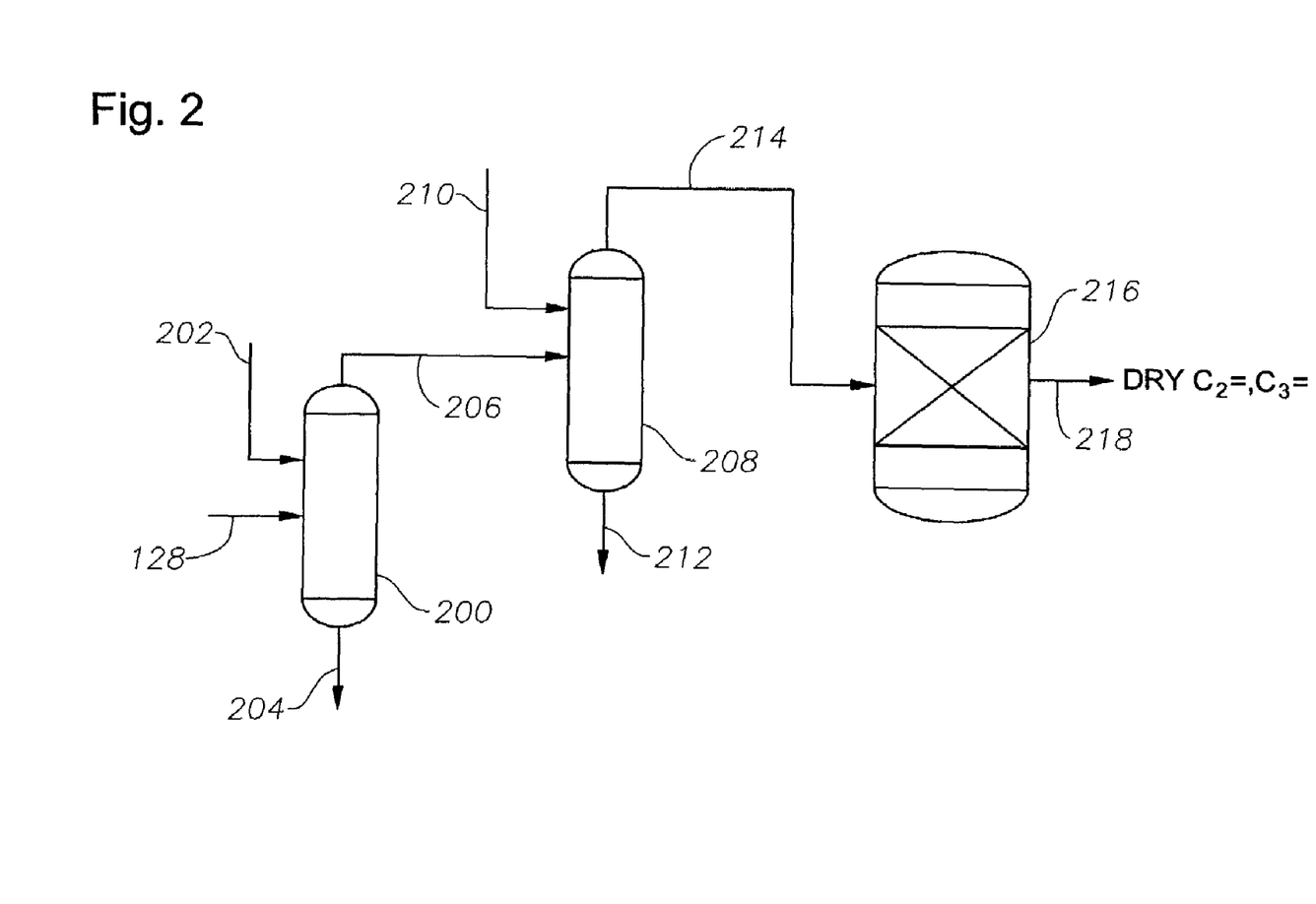
FIG. 2 is a flow diagram showing treatment of ethylene and propylene by caustic wash, water wash, and adsorption.

FIG. 2 shows subsequent treating and drying of the ethylene and propylene containing stream. Ethylene and propylene flow through the line 128 to a caustic wash column 200. A caustic solution is sent through a line 202 to the top portion of the caustic wash column 200 to remove $CO_2$, which is also entrained in the ethylene and propylene containing stream. Spent caustic leaves the caustic wash column 200 through a line 204.

Caustic treated ethylene and propylene exit caustic wash column 200 through a line 206 to a water wash column 208. Water enters the water wash column through a line 210, and water and absorbed components exit the water wash column 208 through a line 212. Water washed ethylene and propylene exit the water was column 208 through a line 214, passing through a dryer 216. Dry ethylene and propylene exit the dryer 216 through a line 218.

Having now fully described this invention, it will be appreciated by those skilled in the art that the invention can be performed within a wide range of parameters within what is claimed, without departing from the spirit and scope of the invention.

What is claimed is:

1. A method of separating dimethyl ether from an olefin stream, comprising:
    contacting oxygenate with a molecular sieve catalyst to form an olefin stream, wherein the olefin stream contains ethylene, ethane, propylene, propane, and dimethyl ether; and
    separating the olefin stream into a first fraction and a second fraction at a pressure of at least 200 psig in a distillation column having trays, wherein the first fraction contains at least a majority of the ethylene and propylene present in the olefin stream, the second fraction contains at least a majority of the dimethyl ether present in the olefin stream, and the olefin stream being separated further contains water in an amount not greater than 5,000 wppm so that free water formation or gas hydration does not significantly impede the separation.

2. The method of claim 1, further comprising contacting the olefin stream formed from contacting the oxygenate with the molecular sieve catalyst with water absorbent prior to separating into the first and second fraction.

3. The method of claim 2, wherein the water absorbent is contacted with the olefan stream at a molar ratio of water absorbent to total olefin of 1:2 to 1:200.

4. The method of claim 1, wherein the pressure is from 200 to 290 psig.

5. The method of claim 4, wherein the pressure is from 250 to 290 psig.

6. The method of claim 1, wherein the first fraction contains at least a majority of the propane present in the olefin stream.

7. The method of claim 1, wherein the first fraction contains not greater than 100 wppm dimethyl ether.

8. The method of claim 1, wherein the second fraction contains at least a majority of the propane present in the olefin stream.

9. The method of claim 1, wherein water absorbent is added to the distillation column.

10. The method of claim 1, wherein the second fraction has an average temperature of not greater than 250° F.

11. The method of claim 10, wherein the second fraction has an avenge temperature of not greater than 240° F.

12. The method of claim 11, wherein the second fraction has an average temperature of not greater than 230° F.

13. The method of claim 9, wherein the water absorbent is added to the distillation column at a molar ratio of water absorbent to total olefin stream to be separated of from 4:1 to 1:5,000.

14. The method of claim 1, wherein the provided olefin stream further comprises $CO_2$, and the first fraction further contains at least a majority of the $CO_2$ in the provided olefin stream.

15. The method of claim 14, further comprising acid gas treating the first fraction.

16. The method of claim 1, wherein the provided olefin stream further comprises $C_4+$ hydrocarbon components, and the second fraction further contains at least a majority of the $C_4+$ hydrocarbon components in the provided olefin stream.

17. The method of claim 1, further comprising separating the ethylene and propylene in the first fraction and polymerizing the ethylene.

18. The method of claim 1, further comprising separating the ethylene and propylene in the first fraction and polymerizing the propylene.

19. The method of claim 1, further comprising contacting the first fraction wit water, acid gas treating the water contacted first fraction, and drying the acid gas treated first fraction.

20. A method of separating dimethyl ether from an olefin stream, comprising:
   contacting oxygenate with a molecular sieve catalyst to form an olefin stream, wherein the olefin stream contains ethylene, ethane, propylene, propane, dimethyl ether and water;
   removing water from the olefin stream so that the olefin stream contains less than 5,000 wppm water; and
   separating the olefin steam containing less than 5,000 wppm water into a first fraction and a second fraction in a distillation column having trays at a pressure of at least 200 psig so that free water formation or gas hydration does not significantly impede the separation, wherein the first fraction contains at least a majority of the ethylene and propylene present in the olefin stream, and the second fraction contains at least a majority of the dimethyl ether present in the olefin stream.

21. The method of claim 20, wherein the water is removed from the olefin stream by contacting the olefin stream with water absorbent at a molar ratio of water absorbent to total olefin of 1:2 to 1:200.

22. The method of claim 20, wherein water absorbent is added to the distillation column.

23. The method of claim 22, wherein the water absorbent is added to the distillation column at a molar ratio of water absorbent to total olefin stream to be separated of from 4:1 to 1:5,000.

24. The method of claim 23, wherein the olefin stream is separated at a pressure of from 200 to 290 psig.

25. The method of claim 20, wherein the provided olefin stream further comprises $CO_2$ and the first fraction further contains at least a majority of the $CO_2$ in the provided olefin stream.

26. The method of claim 25, further comprising acid gas treating the first fraction.

27. The method of claim 20, wherein the provided olefin stream further comprises $C_4+$ hydrocarbon components, and the second fraction further contains at least a majority of the $C_4+$ hydrocarbon components in the provided olefin stream.

28. The method of claim 20, further comprising separating the ethylene and propylene in the first fraction and polymerizing the ethylene.

29. The method of claim 20, farther comprising separating the ethylene and propylene in the first fraction and polymerizing the propylene.

30. The method of claim 20, further comprising contacting the first fraction with water, acid gas treating the water contacted first fraction, and drying the acid gas treated first fraction.

31. The method of claim 2 or 21, wherein the water absorbent is selected from the group consisting of alcohols, amines, amides, nitriles, heterocyclic nitrogen containing compounds, or a combination thereof.

32. The method of claim 2 or 21, wherein the olefin stream being separated contains not greater than 1,000 ppm water.

* * * * *